(12) United States Patent
Kitade et al.

(10) Patent No.: US 7,629,447 B2
(45) Date of Patent: Dec. 8, 2009

(54) DIDEOXYNUCLEOSIDE DERIVATIVES

(75) Inventors: Yukio Kitade, Gifu (JP); Yoshihito Ueno, Gifu (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 203 days.

(21) Appl. No.: 11/678,973

(22) Filed: Feb. 26, 2007

(65) Prior Publication Data

US 2008/0064868 A1 Mar. 13, 2008

(30) Foreign Application Priority Data

Sep. 12, 2006 (JP) ............................. 2006-246844

(51) Int. Cl.
  *C07H 19/06* (2006.01)
  *C07H 19/10* (2006.01)
  *C07H 19/16* (2006.01)
  *C07H 19/20* (2006.01)
  *C07H 21/02* (2006.01)

(52) U.S. Cl. .................... 536/23.1; 536/26.7; 536/26.8; 536/27.6; 536/27.81; 536/28.5; 536/28.53

(58) Field of Classification Search ........................ None
See application file for complete search history.

(56) References Cited

U.S. PATENT DOCUMENTS 4,851,519 A * 7/1989 Lambert et al. ............ 536/28.2
5,010,060 A * 4/1991 Lambert et al. ................ 514/49

FOREIGN PATENT DOCUMENTS

WO    WO 03/093472 A2   11/2003

OTHER PUBLICATIONS (R) Harada et al., "Nucleosides. 139. Synthesis and Anticytomegalovirus and Antiherpes Simplex Virus Activity of 5'-Modified Analogues of 2'-Fluoroarabinosylpyrimidine Nucleosides," Journal of Medicinal Chemistry, 30(1), 226-229 (1987).*
Gryaznov et al., *Nucleic Acids Research*, 20(13): 3403-09 (1992).
Helmling et al., *Nucleosides, Nucleotides & Nucleic Acids*, 22(5-8): 1035-38 (2003).
Kawasaki et al., *J. Med. Chem.*, 36(7): 831-41 (1993).
Obika et al., *Angewandte Chemie International Edition*, 44(13): 1944-47 (Mar. 18, 2005).
Obika et al., *Chem. Commun.*, 2202-03 (2003).
Shi et al., *Bioorganic & Medicinal Chemistry*, 13: 1641-52 (2005).
Ueno et al., The Chemical Society of Japan 86th Spring Convention, Abstract No. 2G3-38 (Mar. 13, 2006).
Kawasaki et al., *J. Med. Chem.*, 36: 831-41 (1993).
Ueno et al., *J. Org. Chem.*, 70: 7925-35 (2005).
Ueno et al., *Tetrahedron*, 64: 11328-34 (2008).

* cited by examiner

*Primary Examiner*—Lawrence E Crane
(74) *Attorney, Agent, or Firm*—Leydig, Voit & Mayer, Ltd.

(57) ABSTRACT

The invention provides a 5'-amino-2'-fluoro-2',5'-dideoxynucleoside compound represented by the formula [1]:

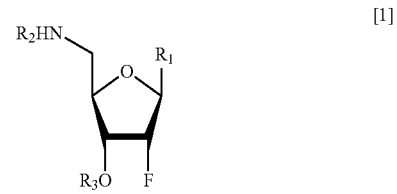

[1]

wherein $R_1$ represents a nucleic acid base which may have a protecting group; $R_2$ represents a hydrogen atom or an amino protecting group; and $R_3$ represents a hydrogen atom or a hydroxyl protecting group. The invention also provides a dideoxynucleoside-insoluble carrier bound substance and an oligonucleotide analogue involving the dideoxynucleoside compound.

6 Claims, 1 Drawing Sheet

```
                        SEQUENCE LISTING

<160> NUMBER OF SEQ ID NOS: 10

<210> SEQ ID NO 1
<211> LENGTH: 17
<212> TYPE: DNA
<213> ORGANISM: Artificial
<220> FEATURE:
<223> OTHER INFORMATION: oligonucleotide analog
<220> FEATURE:
<221> NAME/KEY: misc_feature
<222> LOCATION: (8)..(8)
<223> OTHER INFORMATION: 5'-amino-2'-fluoro-2',5'-dideoxyuridine
<220> FEATURE:
<221> NAME/KEY: modified_base
<222> LOCATION: (8)..(8)
<223> OTHER INFORMATION: 5'-amino-2'-fluoro-2',5'-dideoxyuridine

<400> SEQUENCE: 1
aaggaaanga ggaaaga                                                  17

<210> SEQ ID NO 2
<211> LENGTH: 17
<212> TYPE: DNA
<213> ORGANISM: Artificial
<220> FEATURE:
<223> OTHER INFORMATION: oligonucleotide analog
<220> FEATURE:
<221> NAME/KEY: misc_feature
<222> LOCATION: (7)..(8)
<223> OTHER INFORMATION: 5'-amino-2'-fluoro-2',5'-dideoxyuridine

<400> SEQUENCE: 2
aaggaannga ggaaaga                                                  17

<210> SEQ ID NO 3
<211> LENGTH: 17
```

```
<212> TYPE: DNA
<213> ORGANISM: Artificial
<220> FEATURE:
<223> OTHER INFORMATION: oligonucleotide analog
<220> FEATURE:
<221> NAME/KEY: misc_feature
<222> LOCATION: (8)..(8)
<223> OTHER INFORMATION: 5'-aminothymidine

<400> SEQUENCE: 3
aaggaaanga ggaaaga                                                17

<210> SEQ ID NO 4
<211> LENGTH: 17
<212> TYPE: DNA
<213> ORGANISM: Artificial
<220> FEATURE:
<223> OTHER INFORMATION: oligonucleotide analog
<220> FEATURE:
<221> NAME/KEY: misc_feature
<222> LOCATION: (7)..(8)
<223> OTHER INFORMATION: 5'-aminothymidine

<400> SEQUENCE: 4
aaggaannga ggaaaga                                                17

<210> SEQ ID NO 5
<211> LENGTH: 17
<212> TYPE: DNA
<213> ORGANISM: Artificial
<220> FEATURE:
<223> OTHER INFORMATION: oligonucleotide

<400> SEQUENCE: 5
aaggaaatga ggaaaga                                                17

<210> SEQ ID NO 6
<211> LENGTH: 17
<212> TYPE: DNA
<213> ORGANISM: Artificial
<220> FEATURE:
<223> OTHER INFORMATION: oligonucleotide

<400> SEQUENCE: 6
aaggaattga ggaaaga                                                17

<210> SEQ ID NO 7
<211> LENGTH: 17
<212> TYPE: DNA
<213> ORGANISM: Artificial
<220> FEATURE:
<223> OTHER INFORMATION: oligonucleotide

<400> SEQUENCE: 7
ttcctttact cctttct                                                17

<210> SEQ ID NO 8
<211> LENGTH: 17
<212> TYPE: DNA
<213> ORGANISM: Artificial
<220> FEATURE:
<223> OTHER INFORMATION: oligonucleotide

<400> SEQUENCE: 8
ttccttaact cctttct                                                17

<210> SEQ ID NO 9
```

-continued

```
<211> LENGTH: 17
<212> TYPE: RNA
<213> ORGANISM: Artificial
<220> FEATURE:
<223> OTHER INFORMATION: oligonucleotide

<400> SEQUENCE: 9
uuccuuuacu ccuuucu                                                  17

<210> SEQ ID NO 10
<211> LENGTH: 17
<212> TYPE: RNA
<213> ORGANISM: Artificial
<220> FEATURE:
<223> OTHER INFORMATION: oligonucleotide

<400> SEQUENCE: 10
uuccuuaacu ccuuucu                                                  17
```

DIDEOXYNUCLEOSIDE DERIVATIVES

CROSS-REFERENCE TO RELATED APPLICATIONS

This application claims priority to Japanese Patent Application 2006-246844, filed on Sep. 12, 2006.

TECHNICAL FIELD

The present invention relates to a novel dideoxynucleoside derivative, an amidite reagent using the same, and an oligonucleotide analogue into which said dideoxynucleoside derivative is introduced.

SEQUENCE LISTING

Incorporated by reference in its entirety herein is a computer-readable nucleotide/amino acid sequence listing submitted concurrently herewith and identified as follows: One 2,433 byte ASCII (Text) file named "SequenceListing.TXT," created Feb. 26, 2007.

BACKGROUND OF THE INVENTION

In the following description of the present specification, when nucleic acid bases are referred to, A, C, G, T and U it means adenine, cytosine, guanine, thymine and uracil, respectively. In addition, the term "oligonucleotide" optionally includes "polynucleotide".

It has been known that, when a duplex RNA is introduced into a cell, an mRNA (messenger RNA) having a complementary base sequence to the RNA is decomposed and causes inactivation of the mRNA (RNA interference; abbreviated as "RNAi"). Such phenomenon has been considered to occur by the following mechanism.

That is, when a relatively long duplex RNA (dsRNA) is introduced into a cell, firstly the RNA is decomposed to 21 to 23 bases in size by an RNase III-like nuclease referred to as Dicer, and generates low molecular weight siRNA. Then, the siRNA binds to plural number of proteins to form a complex referred to as RISC (RNA induced silencing complex). The resulting complex recognizes and binds to an mRNA of the cell in which the same base sequence as the siRNA is contained, and then the mRNA is cleaved at the central part of siRNA. It has been considered that, in consequence, the relevant gene is inactivated.

The RNAi method (the RNA interference method) is a method to suppress an expression of a certain gene by introducing an artificially synthesized RNA into a cell utilizing this phenomenon, and has been used widely as a simple and potential method for inhibiting a gene function (see, for example, Fire, A. et. al., Nature, 1998, vol. 391, pp. 806-811; Svobada, P. et al., Development, 2000, vol. 127, pp. 4147-4156; Elbashir, S. M., Lendeckel, W. and Tuschl, T., Genes and Dev., 2001, vol. 15, pp. 188-200; Zamore, P. D. et al., Cell, 2000, vo. 101, pp. 25-33; Bernstein, E. et al., Nature, 2001, vol. 409, pp. 363-366).

In addition, compared to the antisense method described later, the RNAi method has advantages such as capability of suppressing the gene expression efficiently by a low concentration due to use of a mechanism possessed by living individual; low toxicity; high specificity to the target base sequence; and the simple experimental procedures. Also, the method has been used widely for knock-down of an endogenous gene in a cell. Further, an application of the method to gene therapy based on the specific decomposition of mRNA coding an abnormal gene has been expected.

On the other hand, however, the conventionally used low molecular weight RNA such as dsRNA and siRNA has a problem of difficulty in handling, because they are easily decomposed by an action of nucleic acid-hydrolyzing enzymes such as nucleases.

On the other hand, as an another method for controlling a gene expression, a technique named antisense method has also been known.

A base sequence of an mRNA for synthesis of a protein (for directing protein synthesis) is referred to as a sense sequence, and a complementary base sequence thereto is referred to as an antisense. In addition, a nucleic acid having a base sequence of an antisense is referred to as an antisense nucleic acid.

The antisense method is one of the methods for controlling an expression of a gene that are intended to suppress only a target gene specifically to the base sequence by administering the antisense nucleic acid being complementary to an mRNA transcripted from the certain target gene to the cell, and thereby forming a duplex between the mRNA of the cell and the antisense nucleic acid administered. Function of the target gene can be analyzed by evaluating inhibitory effect of the antisense nucleic acid on the target gene.

In addition, the antisense method can be applied to pharmaceutical field. For example, by binding an antisense nucleic acid to an mRNA, which is involved in synthetic process of a responsible protein factor for developing certain kind of disease, it can be expected that the function of the relevant gene will be prevented. Therefore, it is expected that, by using an antisense nucleic acid, treatment based on inhibition of action of causative gene for a disease can be performed. For example, Formivirsen, a medical drug for cytomegalovirus retinitis, which has been currently approved to ISIS Pharmaceuticals Inc. by FDA in the United States, is one example of this technology.

Properties required for the antisense nucleic acid include, for example, capability of forming a stable duplex with target RNA; base sequence-recognizing ability not to bind to a sequence containing mismatch base; resistance to nucleases; and cell membrane permeability. In addition, for using the antisense nucleic acid as a medical drug, recognition specificity to the base sequence, resistance to nucleases, antimetabolic property and intracellular mobility are of importance.

However, if naturally occurring type of oligonucleotide is used as an antisense nucleic acid, there are some problems that, for example, the required properties as described above including resistance to nucleases cannot be satisfied.

Therefore, up to the present, a number of trials on the modifications of nucleic acid have been conducted in order to obtain an oligonucleotide having properties of overcoming the drawback of the naturally occurring type of oligonucleotide, and also having properties being satisfied. This includes, for example, modification of base part of a nucleic acid (N. Haginoya et al., Bioconjugate Chem., 1997, vol. 8, pp. 271-280), modification of a ribose (M. Aoyagi et al., Bioorg. Med. Chem. Lett., 1996, vol. 6, pp. 1573-1576), alteration of a ribose ring itself (A. Kakefuda et al., Tetrahedron, 1996, vol. 52, pp. 2863-2876), modification to phosphodiester (M. Shimizu et al., 2006, vol. 71, pp. 4262-4269) and alteration of phosphodiester bond (A. Waldner et al., Bioorg. Med. Chem. Lett., 1994, vol. 4, pp. 405-408). By combining these techniques, diversification of the antisense nucleic acid, which can satisfy the properties as described above, can be expected. For example, S. M. Gryaznov et al. have synthesized 5'-phosphoroamidate type DNA (S. M.

Gryaznov et al., Nucleic Acids Res., 1992, vol. 20, pp. 3403-3409). This type of DNA has resistance to nucleic acid degrading enzymes such as nucleases, but there remains a problem that binding affinity thereof to target mRNA is insufficient. To solve the problem of binding affinity to the target mRNA, S. Obika et al. have synthesized 5'-amino-2',4'-bridged nucleic acid (BNA) containing a nucleotide which is constructed by introducing amino group at 5'-position of the sugar moiety and 2'- and 4'-positions are cyclized via an oxygen atom (S. Obika, et. al., Chem. Commun., 2003, pp. 2202-2203). In addition, Obika et al. also have synthesized 5'-amino-3',5'-BNA in which 5'-amino group and 3'-position are bridged by methylene group (S. Obika, et al., Angew. Chem. Int. Ed., 2005, vol. 44, pp. 1945-1947). These BNAs have high binding affinity to target mRNA and resistance to nucleic acid degrading enzymes such as nucleases. However, there has not been any report on the protein suppression activity when these BNAs are introduced into siRNA.

BRIEF SUMMARY OF THE INVENTION

The present invention has been made considering the above-described circumstances, and an object of the invention is to provide a novel dideoxynucleoside derivative which is suitable as a raw material for the synthesis of antisense nucleic acids, and to provide an oligonucleotide analogue being introduced with the aforementioned dideoxynucleoside derivative which possess thermal stabilities.

The present invention has been made to solve the above-mentioned problems, and is constituted by the following items.

(1) A 5'-Amino-2'-fluoro-2',5'-dideoxynucleoside derivative represented by the following formula [1]:

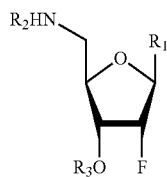

(wherein R₁ represents a nucleic acid base which may have a protecting group; R₂ represents a hydrogen atom or a protecting group of an amino group; R₃ represents a hydrogen atom or a protecting group of a hydroxyl group).

(2) A dideoxynucleoside-insoluble carrier bound substance prepared by binding a 5'-amino-2'-fluoro-2',5'-dideoxynucleoside derivative represented by the following formula [6]:

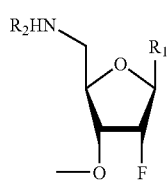

(wherein R₁ represents a nucleic acid base which may have a protecting group; R₂ represents a hydrogen atom or a protecting group of an amino group), to an insoluble carrier.

(3) An oligonucleotide analogue being introduced with a 5'-amino-2'-fluoro-2',5'-dideoxynucleoside derivative represented by the following formula [1]:

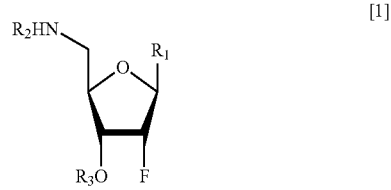

(wherein R₁ represents a nucleic acid base which may have a protecting group; R₂ represents a hydrogen atom or a protecting group of an amino group; R₃ represents a hydrogen atom or a protecting group of a hydroxyl group).

BRIEF DESCRIPTION OF THE SEVERAL VIEW OF THE DRAWING

Description of Codes

Figure 1:
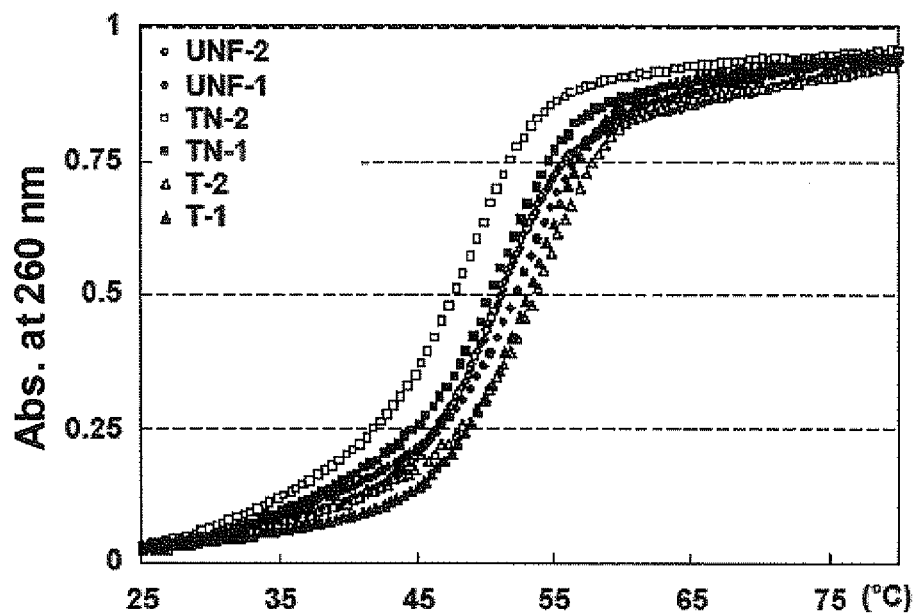
FIG. 1 shows the results of thermal stability test carried out for the duplexes DNA/DNA obtained in Example 3 and Comparative Example 3.

In FIG. 1, closed triangle (▲) indicates the results on the duplex DNA/DNA obtained by using T-1 (control); open triangle (△) indicates the results on the duplex DNA/DNA obtained by using T-2 (control); closed circle (●) indicates the results on the duplex DNA/DNA obtained by using NF-1; open circle (○) indicates the results on the duplex DNA/DNA obtained by using UNF-2; closed square (■) indicates the results on the duplex DNA/DNA obtained by using TN-1; open square (□) indicates the results on the duplex DNA/DNA obtained by using TN-2.

Figure 2:
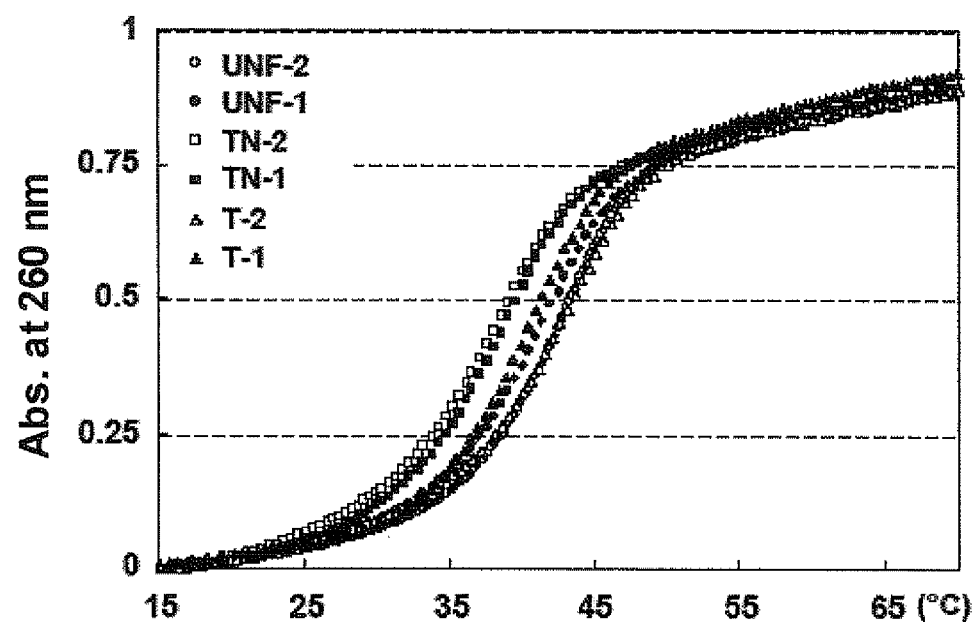
FIG. 2 shows the results of thermal stability test carried out for the duplexes DNA/RNA obtained in Example 4 and Comparative Example 4.

In FIG. 2, closed triangle (▲) indicates the results on the duplex DNA/RNA obtained by using T-1 (control); open triangle (△) indicates the results on the duplex DNA/RNA obtained by using T-2 (control); closed circle (●) indicates the results on the duplex DNA/RNA obtained by using UNF-1; open circle (○) indicates the results on the duplex DNA/RNA obtained by using UNF-2; closed square (■) indicates the results on the duplex DNA/RNA obtained by using TN-1; open square (□) indicates the results on the duplex DNA/RNA obtained by using TN-2.

DETAILED DESCRIPTION OF THE INVENTION

Namely, the present inventors have intensively studied aiming at synthesis of a novel oligonucleotide, which is stable and also applicable to the antisense method and the RNAi method.

There are mainly A-form and B-form in the duplex helical conformation of the nucleic acid. In a single strand state, steric conformation of the nucleic acid fluctuates, whereas, the conformation such as A-form and B-form is fixed by hybridizing the single strand with a complementary sequence chain. To take A-form helical conformation, a nucleic acid in which the conformation of the sugar moiety has been fixed to N-type (C3'-endo) is required. Contrary to this, to take B-form helical conformation, a nucleic acid in which the conformation of the sugar moiety has been fixed to S-type (C2'-endo) is required. A DNA-DNA duplex tends to adopt B-form conformation, and a RNA-RNA duplex tends to adopt A-form conformation. In addition, in the case of a RNA-DNA duplex, it adopts A-form conformation.

The present inventors considered that stability (binding affinity) of a duplex formed between an antisense nucleic acid and a complementary RNA could be improved by fixing the conformation of an antisense nucleic acid to A-type namely, by fixing the conformation of the sugar moiety in the nucleoside which constitutes the antisense nucleic acid to be N-type (3'-endo), because the target was RNA in the case of an antisense nucleic acid.

In addition, based on the knowledge that fixation of the conformation of the sugar moiety in nucleoside, which constitutes DNA, to N-type by introducing an electron-withdrawing substituent at the 2'-position of the sugar moiety has an effect to stabilize the duplex formed between the DNA and a complementary chain (A. M. Kawasaki et al., J. Med. Chem., 1993, vol. 36, pp. 831-841), the present inventors assumed that if an electron-withdrawing fluorine atom was introduced at the 2'-position of the sugar moiety in 5'-amino-type nucleoside, the conformation of the sugar moiety in the nucleoside could be fixed to N-type, and by fixing the conformation, stability of the above-mentioned duplex could be improved.

As a nucleoside derivative in which a fluorine atom is introduced in the sugar moiety, for example, 2'-fluoro-L-uridine, 2'-fluoro-L-cytidine phosphoramidite (S. Helmling et al., Nucleosides, Nucleotides & Nucleic Acids, 2003, vol. 22, Nos. 5-8, pp. 1035-1038, WO 03/093472), D- and L-2'-deoxy-2'-fluororibonucleoside (J. Shi et al., Bioorg. Med. Chem., 2005, vol. 13, pp. 1641-1652) have been known up to now.

Further, it has been reported that resistance to nucleases of duplex nucleic acid is improved by changing phosphodiester bond in an oligonucleotide to phosphoramidate bond (S. M. Gryaznov et al., Nucleic Acids Res., 1992, vol. 20, pp. 3403-3409). However, there is a problem that stability (binding affinity) of a duplex formed between an oligonucleotide having 5'-phosphoramidate bond and a complementary chain thereof is lower compared to that of a duplex formed between an oligonucleotide having only phosphodiester bond.

The present inventors have, therefore, conducted further intensive studies, assuming that a nucleotide having resistance to nucleases and also satisfactory stability (binding affinity) of a duplex nucleic acid formed with a complementary chain thereof can be attained by introducing the above-described two modifications into an oligonucleotide. As a result, a 5'-amino-2'-fluoro-2',5'-dideoxynucleoside derivative being introduced with a —NH— group into the 5'-position and a fluorine atom into the 2'-position in the sugar moiety was synthesized. Subsequently, an oligonucleotide analogue introduced with the above-mentioned dideoxynucleoside derivative was synthesized according to the conventional method. Then, stabilities of the duplex nucleic acid formed between the oligonucleotide analogue and a complementary DNA chain thereof and also a complementary RNA chain thereof were determined. This revealed that the duplex nucleic acid formed between the oligonucleotide analogue being introduced with a 5'-amino-2'-fluoro-2',5'-dideoxynucleoside derivative and a complementary nucleic acid thereof had been improved in thermal stability, and also the binding affinity of the duplex was satisfactory, and thus the present invention was accomplished. Further, since the oligonucleotide analogue has a phosphoramidate bond, it can be anticipated that the aforementioned oligonucleotide analogue and the duplex nucleic acid using the same have high resistance to nucleases.

The dideoxynucleoside derivative of the present invention is a 5'-amino-2'-fluoro-2',5'-dideoxynucleoside derivative represented by the following formula [1]:

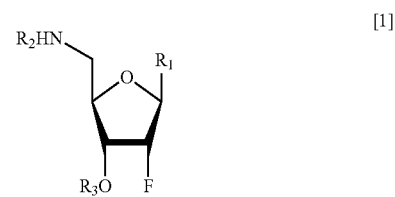

[1]

(wherein $R_1$ represents a nucleic acid base which may have a protecting group; $R_2$ represents a hydrogen atom or a protecting group of an amino group; $R_3$ represents a hydrogen atom or a protecting group of a hydroxyl group;)

(hereafter abbreviated as "dideoxynucleoside derivative of the present invention").

In the formula [1], a nucleic acid base of the nucleic acid base which may have a protecting group represented by $R_1$ includes, besides a naturally-occurring type nucleic acid base selected from adenine, guanine, cytosine, thymine and uracil, minor components of a nucleic acid such as 1-methyladenine, 1-methylguanosine, xanthine, 5-methylcytosine and dihydrouracil and an artificial nucleic acid base such as 6-methoxypurine, 2-aminopurine and pseudo-isocytosine.

In addition, the above-described nucleic acid base may be appropriately protected by a protecting group, which is well known per se and commonly used in the nucleic acid synthesis, if necessary. Specifically, the protecting group includes, but not limited to, for example, a protecting group of amino group such as benzoyl group and acetyl group.

The protecting group of amino group in $R_2$ includes a protecting group of amino group commonly used in this field for nucleoside synthesis. More specifically, for example, 4-Methoxytriphenylmethyl (MMTr) group, 4,4'-Dimethoxytriphenylmethyl (DMTr) group and triphenylmethyl (Tr) group are included.

The protecting group of hydroxyl group in $R_3$ includes a protecting group of hydroxyl group commonly used in this field for the nucleoside synthesis. More specifically, for example, 4,4'-dimethoxytriphenylmethyl group, 2-cyanoethoxyldiisopropylaminophosphinyl group and tert-butyldimethylsilyl group are included.

The dideoxynucleoside derivative of the present invention includes, for example, a compound represented by the following formula [2]:

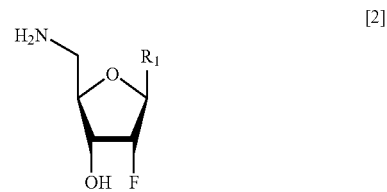

[2]

(wherein $R_1$ represents a nucleic acid base which may have a protecting group). With respect to the nucleic acid base which may have a protecting group represented by $R_1$, specific examples of the protecting group and the nucleic acid base are as described above.

Specific examples of the compound represented by the formula [2] include, for example: 5'-amino-2'-fluoro-2',5'-dideoxyuridine; 5'-amino-2'-fluoro-2',5'-dideoxyadenosine; 5,-amino-2'-fluoro-2',5'-dideoxyguanosine; 5,-amino-2'-fluoro-2',5'-dideoxycytidine; and 5'-amino-2'-fluoro-2',5'-dideoxythymidine.

An another example of the dideoxynucleoside derivative of the present invention includes, for example, a compound represented by the following formula [3]:

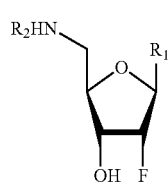

[3]

(wherein $R_1$ represents a nucleic acid base which may have a protecting group; $R_2$ represents a hydrogen atom or a protecting group of amino group). Specific examples of the protecting group and the nucleic acid base with respect to the nucleic acid base which may have a protecting group represented by $R_1$, and specific examples of the protecting group of amino group in $R_2$ are as described above.

Specific examples of the compound represented by the formula [3] include, for example:
5'-amino-2'-fluoro-2',5'-dideoxy-5'-N-monomethoxytrityluridine;
5'-amino-2'-fluoro-2',5'-dideoxy-5'-N-monomethoxytrityladenosine;
5'-amino-2'-fluoro-2',5'-dideoxy-5'-N-monomethoxytritylguanosine;
5'-amino-2'-fluoro-2',5'-dideoxy-5'-N-monomethoxytritylcytididine; and
5'-amino-2'-fluoro-2',5'-dideoxy-5'-N-monomethoxytritylthymidine.

Another example of the dideoxynucleoside derivative of the present invention includes, for example, a compound represented by the following formula [4]:

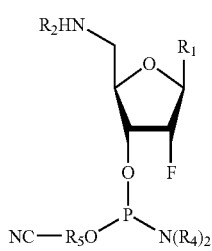

[4]

(wherein $R_1$ represents a nucleic acid base which may have a protecting group; $R_2$ represents a hydrogen atom or a protecting group of an amino group; two $R_4$ represent each independently a lower alkyl group with 1 to 5 carbon atoms; $R_5$ represents a lower alkylene group with 1 to 3 carbon atoms).

Specific examples of the substituent and the nucleic acid base with respect to the nucleic acid base which may have a substituent represented by $R_1$, and specific examples of the protecting group of amino group represented by $R_2$ are as described above.

Specific examples of the lower alkyl group with 1 to 5 carbon atoms represented by $R_4$ include, for example, ethyl group, propyl group and isopropyl group.

Specific examples of the lower alkylene group with 1 to 3 carbon atoms represented by $R_5$ include, for example, ethylene group and propylene group.

Another example of the dideoxynucleoside derivative of the present invention include, for example, a compound represented by the following formula [5]:

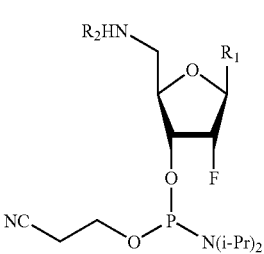

[5]

(wherein $R_1$ represents a nucleic acid base which may have a protecting group; $R_2$ represents a hydrogen atom or a protecting group of an amino group; i-Pr represents an isopropyl group). Specific examples of the substituent and the nucleic acid base with respect to the nucleic acid base which may have a substituent represented by $R_1$, and specific examples of the protecting group of amino group represented by $R_2$ are as described above.

The compounds represented by the formula [4] and the formula [5] can be used as a so-called amidite reagent in the nucleic acid synthesis.

Specific examples of the compound represented by the formula [5] include, for example:
5'-amino-N-monomethoxytrityl-2',5'-dideoxy-2'-fluorouridine-3'-O-[(2-cyanoethyl)-(N,N-diisopropyl)]-phosphoramidite;
5'-amino-N-monomethoxytrityl-2',5'-dideoxy-2'-fluoroadenosine-3'-O-[(2-cyanoethyl) -(N,N-diisopropyl)]-phosphoramidite;
5'-amino-N-monomethoxytrityl-2',5'-dideoxy-2'-fluoroguanosine-3'-O-[(2-cyanoethyl) -(N,N-diisopropyl)]-phosphoramidite;
5'-amino-N-monomethoxytrityl-2',5'-dideoxy-2'-fluorocytidine-3'-O-[(2-cyanoethyl) -(N,N-diisopropyl)]-phosphoramidite; and
5'-amino-N-monomethoxytrityl-2',5'-dideoxy-2'-fluorothymidine-3'-O-[(2-cyanoethyl) -(N,N-diisopropyl)]-phosphoramidite.

Synthesis method of the dideoxynucleoside derivative of the present invention includes, for example, the following procedure.

First, a nucleic acid base as a starting material is cyclized between the carbonyl group of the base moiety and the 2'-hydroxyl group of the sugar moiety using a condensing agent such as diphenyl carbonate ((PhO)$_2$CO) to obtain 2,2'-anhydro-1-β-D-arabinofuranosylnucleoside.

After that, 3',5'-hydroxyl groups of 2,2'-anhydro-1-β-D-arabinofuranosylnucleoside are tritylated by reacting with a tritylating agent such as 4,4'-dimethoxytrityl chloride (DMTrCl) in the presence of a catalyst such as 4-dimethylaminopyridine (DMAP) under the inert gas atmosphere, to obtain 2,2'-anhydro-3',5'-di-O-(4,4'-dimethoxytrityl)-1-β-D-arabinofuranosylnucleoside.

Subsequently, the nucleoside is subjected to ring-opening reaction using a base such as NaOH to obtain 3',5'-di-O-(4,4'-dimethoxytrityl)-nucleoside.

Further, the nucleoside is fluorinated at the 2'-position in the sugar moiety of 3',5'-di-O-(4,4'-dimethoxytrityl)-nucleoside by reacting with a fluorinating agent such as (dimethylamino)sulfur trifluoride (DAST) under the inert gas atmosphere, to obtain 2'-deoxy-3',5'-di-O-(4,4'-dimethoxytrityl)-2'-fluoronucleoside.

After that, the product is de-tritylated at the 3'-position in the sugar moiety by reacting with an acid such as acetic acid to obtain 2'-fluoro-2',5'-dideoxynucleoside.

The resulting 2'-fluoro-2',5'-dideoxynucleoside is azidized via bromination at the 5'-hydroxyl group of the sugar moiety using sodium azide, triphenylphosphine ((Ph)$_3$P) and CBr$_4$ under the inert gas atmosphere, to obtain 5'-azide-2'-fluoro-2',5'-dideoxynucleoside.

The resulting 5'-azide-2'-fluoro-2',5'-dideoxynucleoside is reacted under H$_2$ atmosphere in the presence of a catalyst such as palladium carbon (Pd—C) to obtain 5'-amino-2'-fluoro-2',5'-dideoxynucleoside of the present invention represented by the following formula [2]:

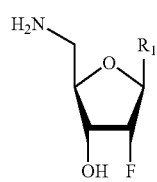

[2]

(wherein R$_1$ represents a nucleic acid base which may have a protecting group.)

Next, according to the method which is well known per se and has been described, for example, in S. Obika et al., Angew. Chem. Int. Ed., 2005, vol. 44, pp. 1944-1947, 5'-amino-2'-fluoro-2',5'-dideoxynucleoside represented by the formula [2] is tritylated by reacting with a tritylating agent such as 4-methoxytriphenylmethyl chloride (MMTrCl) in the presence of a catalyst such as DMAP to obtain 5'-amino-2'-fluoro-2',5'-dideoxy-5'-N-monoethoxytritylnucleoside represented by the following formula [3]:

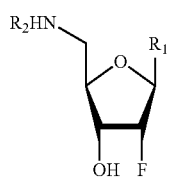

[3]

(wherein R$_1$ represents a nucleic acid base which may have a protecting group; R$_2$ represents a hydrogen atom or a protecting group of amino group.)

Subsequently, the resulting 5'-amino-2'-fluoro-2',5'-dideoxy-5'-N-monoethoxytritylnucleoside is phosphorylated by reacting with a phosphorylating agent such as 2-cyanoethyldiisopropylchloro-phosphoramidite (i-Pr$_2$ NP(Cl)OCE) in the presence of a base such as diisopropylethylamine (DIPEA) to obtain 5'-amino-N-monoethoxytrityl-2'-fluoro-2',5'-dideoxynucleoside amidite unit represented by the following formula [5]:

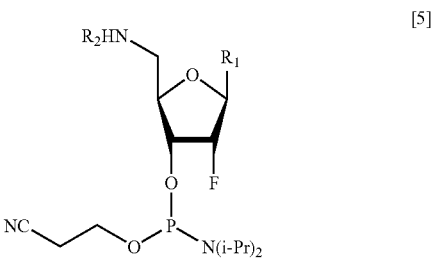

[5]

(wherein R$_1$ represents a nucleic acid base which may have a protecting group; R$_2$ represents a hydrogen atom or a protecting group of an amino group; i-Pr represents an isopropyl group.)

Next, synthesis method of the dideoxynucleoside derivative of the present invention will be described more specifically, using an example where R$_1$ in the formula [1] is uracil. Scheme of the synthesis method will be shown below (Synthesis Scheme A).

Formal names of the abbreviations used in the Synthesis Scheme A described below are as follows;

(PhO)$_2$CO: diphenyl carbonate

DMF: N,N-dimethylformamide

DMTrCl: 4,4'-dimethoxytrityl chloride

DMAP: 4-dimethylaminopyridine

MeOH: methanol

DAST: (diethylamino) sulfur trifluoride

AcOH: acetic acid (Ph)$_3$P: triphenylphosphine

Pd/C: palladium carbon

MMTrCl: 4-methoxytriphenylmethyl chloride i-Pr$_2$NP(Cl)OCE: 2-cyanoethyldiisopropylchloro-phosphoramidite i-Pr$_2$ Net: diisopropylethylamine.

[Reaction Scheme A]

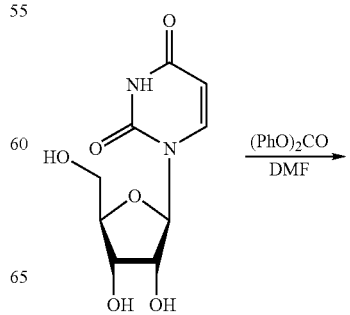

-continued

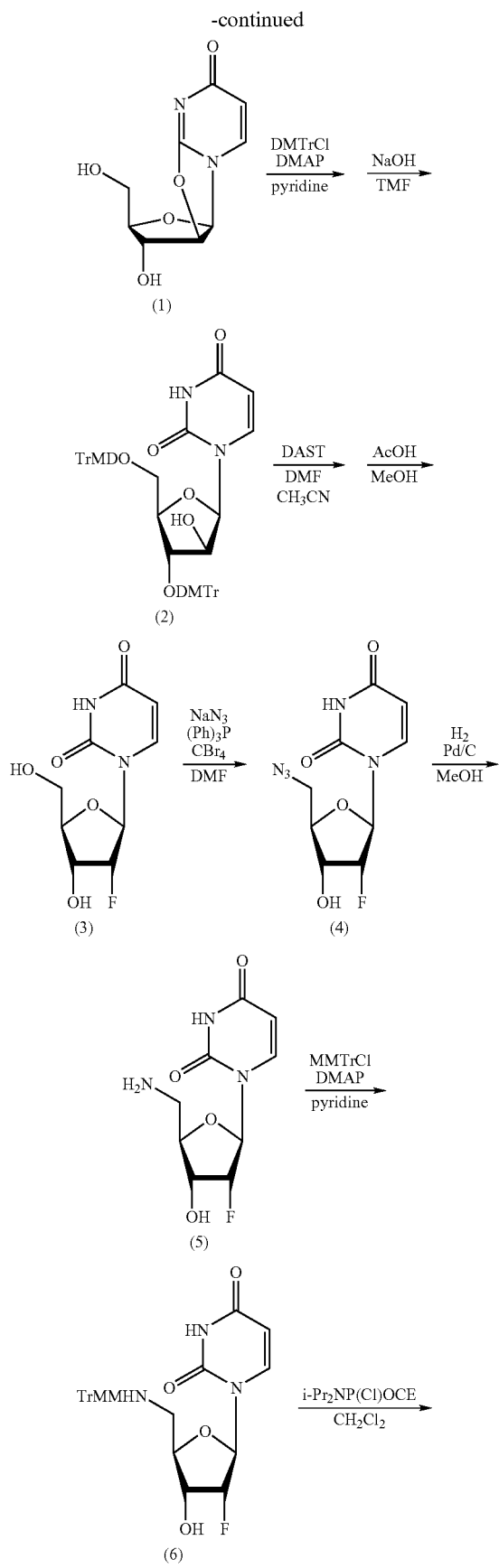

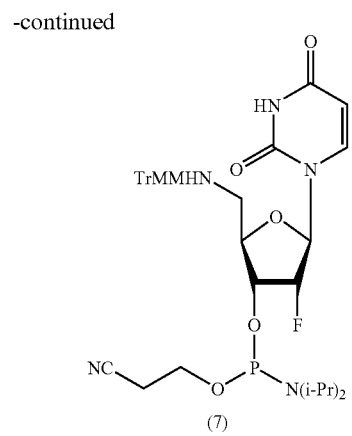

First, uridine as a starting material is cyclized using diphenyl carbonate ((PhO)$_2$CO) as a condensing agent to obtain 2,2'-anhydro-1-β-D-arabinofuranosyluridine (1) ((1) means a compound represented by (1) in the above described Reaction Scheme A, hereinafter, same as above).

After that, the 3',5'-hydroxyl groups of 2,2'-anhydro-1-β-D-arabinofuranosyluridine (1) are tritylated by reacting with 4,4'-dimethoxytrityl chloride (DMTrCl) in the presence of 4-dimethylaminopyridine (DMAP) as a catalyst under the argon (Ar) atmosphere, to obtain 2,2'-anhydro-3',5'-di-O-(4,4'-dimethoxytrityl)-1-β-D-arabinofuranosyluridine (not shown in the Scheme).

Subsequently, the resulting compound is subjected to ring-opening reaction using NaOH (40 mL) to obtain 3',5'-di-O-(4,4'-dimethoxytrityl)-uridine (2).

Further, 3',5'-di-O-(4,4'-dimethoxytrityl)-uridine (2) is fluorinated at the 2'-position in the sugar moiety by reacting with (diethylamino) sulfur trifluoride (DAST) under the argon (Ar) atmosphere, to obtain 2'-deoxy-3',5'-di-O-(4,4'-dimethoxytrityl)-2'-fluorouridine (not shown in the Scheme).

After that, the product is de-tritylated at the 3'-position in the sugar moiety by reacting with acetic acid, to obtain 2'-fluoro-2',5'-dideoxyuridine (3).

The resulting 2'-fluoro-2',5'-dideoxyuridine (3) is azidized at the 5'-hydroxyl group of the sugar moiety by reacting together with sodium azide, triphenylphosphine ((Ph)$_3$P) and CBr$_4$ under the Ar atmosphere, to obtain 5'-azide-2'-fluoro-2',5'-dideoxyuridine (4).

The resulting 5'-azide-2'-fluoro-2',5'-dideoxyuridine (4) is reacted under the H$_2$ atmosphere in the presence of a catalyst such as palladium carbon (Pd—C) to obtain the objective 5'-amino-2'-fluoro-2',5'-dideoxyuridine (5).

Next, the resulting 5'-amino-2'-fluoro-2',5'-dideoxyuridine (5) is tritylated by reacting with 4-methoxytriphenylmethyl chloride (MMTrCl) in the presence of DMAP to obtain 5'-amino-2'-fluoro-2',5'-dideoxy-5'-N-monomethoxytrityluridine (6).

Subsequently, the resulting 5'-amino-2'-fluoro-2',5'-dideoxy-5'-N-monomethoxytrityluridine is phosphorylated by reacting with 2-cyanoethyldiisopropylchloro-phosphoramidite (i-Pr$_2$NP(Cl)OCE) in the presence of diisopropylethylamine (DIPEA), to obtain 5'-amino-N-monomethoxytrityl-2'-fluoro-2',5'-dideoxyuridine-3'-O-[(2-cyanoethyl)-(N,N-diisopropyl)]-phosphoramidite (7) having a phosphorous group.

The insoluble carrier used for the dideoxynucleoside-insoluble carrier bound substance of the present invention is not particularly limited, so long as the carrier is those commonly used in this field, and includes, for example, polystyrene and glass beads. In particular, CPG (controlled pore glass) that is powdered porous glass beads is commonly preferably used.

Specific example of the dideoxynucleoside-insoluble carrier bound substance of the present invention is one in which the nucleoside derivative of the present invention, namely, 5'-amino-2'-fluoro-2',5'-dideoxynucleoside derivative represented by the following formula [1]:

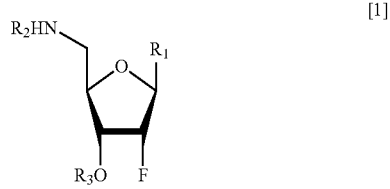

(wherein $R_1$ represents a nucleic acid base which may have a protecting group; $R_2$ represents a hydrogen atom or a protecting group of an amino group; $R_3$ represents a hydrogen atom or a protecting group of a hydroxyl group;) is bound at the 3-O-position of pentose thereof to the surface of CPG via spacer of an organic molecule such as succinic acid by an ester linkage.

Namely, the dideoxynucleoside-insoluble carrier bound substance of the present invention is a substance in which 5'-amino-2'-fluoro-2',5'-dideoxynucleoside derivative represented by the following formula [6]:

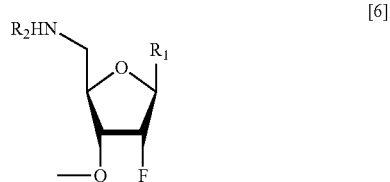

(wherein $R_1$ represents a nucleic acid base which may have a protecting group; $R_2$ represents a hydrogen atom or a protecting group of an amino group;) is bound to an insoluble carrier via a suitable spacer, if necessary. In formula [6], specific examples of the substituent and the nucleic acid base with respect to the nucleic acid base which may have a substituent represented by $R_1$, and specific examples of the protecting group of amino group in $R_2$ are as described above.

The dideoxynucleoside-insoluble carrier bound substance prepared by binding the dideoxynucleoside derivative of the present invention to an insoluble carrier can be used as a starting material used in the method well known per se for solid-phase synthesis of nucleic acids.

The method for binding the dideoxynucleoside derivative of the present invention to an insoluble carrier (for example, CPG) includes the methods, which are well known per se and have been described, for example, in R. Kierzek et al., Biochemistry, 1986, vol. 25, pp. 7840-7846.

In addition, the dideoxynucleoside derivative of the present invention can be also used as a starting material for preparing oligonucleotide analogues.

Production of the oligonucleotide analogues, into which the dideoxynucleoside derivative of the present invention is introduced, can be performed according to the method of chemical synthesis processes well known per se, except using the dideoxynucleoside derivative of the present invention as a starting material. For example, using a DNA synthesizer, an oligonucleotide analogue is synthesized according to the ordinary phosphoramidite method or the solid-phase phosphoramidite method (R. Kierzek et al., Biochemistry, 1986, vol. 25, pp. 7840-7846) which are commonly employed for DNA synthesis, and then purified by a conventional method using anion-exchange column chromatography to obtain the objective oligonucleotide analogue being introduced with the dideoxynucleoside derivative of the present invention.

In addition, the duplex nucleic acids (DNA/DNA, DNA/RNA, RNA/RNA) containing the oligonucleotide analogue being introduced with the dideoxynucleoside derivative of the present invention may be synthesized according to the method well known per se. Also, these duplexes can be produced using commercially available kits.

Since conformation of the sugar moiety in the dideoxynucleoside derivative of the present invention is regulated to be N-type by introducing a fluorine atom into the 2'-position of the sugar moiety thereof as described previously, the duplex nucleic acid obtained by using the oligonucleotide analogue being introduced with the dideoxynucleoside derivative of the present invention is one in which the duplex chain has been improved in thermal stability and has satisfactory binding affinity. In addition, the dideoxynucleoside derivative of the present invention is introduced with a —NH— group at the 5'-position of the sugar moiety thereof. Consequently, when an oligonucleotide analogue is synthesized using the nucleoside derivative, the nucleotide derived from the above dideoxynucleoside derivative binds to the neighboring nucleotide via phosphoramidate linkage. By this reason, in the oligonucleotide analogue being introduced with the above dideoxynucleoside derivative, the phosphodiester linkage at the part where dideoxynucleoside derivative is introduced is replaced by a phosphoramidate linkage. From this reason, the duplex nucleic acid obtained by using the oligonucleotide analogue is expected to have improved resistance to nucleases.

Further, due to the above-mentioned properties, the oligonucleotide analogue being introduced with the dideoxynucleoside derivative of the present invention can be used as an excellent antisense nucleic acid in the antisense method. Also, the duplex nucleic acid (DNA/DNA, DNA/RNA and RNA/RNA) containing using this oligonucleotide analogue can be used as siRNA or dsRNA in the RNAi method. Furthermore, application to pharmaceutical field can be expected.

The oligonucleotide analogue being introduced with a 5'-amino-2'-fluoro-2',5'-dideoxynucleoside derivative of the present invention has excellent thermal stability and also high binding affinity when duplex is formed. Also, it is anticipated that it has high resistance to nucleases. Further, the 5'-amino-2'-fluoro-2',5'-dideoxynucleoside derivative of the present invention can be used as an amidite reagent to be used for nucleic acid synthesis, and also as a starting material for solid phase synthesis of nucleic acid by binding the amidite reagent to a solid phase.

The present invention will be described hereinbelow in more detail with Examples and Comparative Examples, which do not constitute limiting aspects of the present invention.

EXAMPLES (1) Laboratory Equipment

In each Example and Comparative Example, the following sets of laboratory equipment were used.

Syntheses of DNA and RNA were carried out using 3400 DNA Synthesizer (a nucleic acid synthesizer produced by Applied Biosystems).

Measurements of NMR spectra were carried out using JEOL JNM AL400 spectrometer (produced by JEOL DATUM LTD.).

(2) In each Example and Comparative Example, the following reagents were used.
Uridine: SIGMA, produced by Sigma Ardrich Corp.
Thymidine: SIGMA, produced by Sigma Ardrich Corp.
Palladium charcoal: produced by Nacalai Tesque, Inc.
4-Methoxytriphenylmethyl chloride: produced by Tokyo Chemical Industry Co., Ltd.
Diisopropylethylamine: produced by Wako Pure Chemical Industries, Ltd.
Diphenyl carbonate, dichloromethane (dehydrated), pyridine: produced by Wako Pure Chemical Industries, Ltd.
N,N-dimethylformamide, sodium chloride, palladium carbon (Pd—C), acetic anhydride: produced by Nacalai Tesque, Inc.
Chloroform: produced by Tokuyama Corp.
Purification grade chloroform: Chloroform-d, 99.8 atom % D (ALDRICH, produced by Sigma Ardrich Corp.)
Ethyl acetate, n-hexane, methanol: produced by Sankyo Chemical Co., Ltd.
4-Dimethylaminopyridine: produced by Tokyo Chemical Industry Co., Ltd.
4,4'-Dimethoxytrityl chloride, (diethylamino) sulfur trifluoride: produced by Sigma Aldrich Corp.
Tetrahydrofuran: produced by Kanto Chemical Co., Inc.
Silica gel for column chromatography: Silica gel 60N, spherical, neutral (produced by Kanto Chemical Co., Inc.)
2-Cyanoethyldiisopropylchloro-phosphoramidite unit: produced by Lancaster Synthesis (3) In each Example and Comparative Example, the following abbreviations were used.
(PhO)$_2$CO: diphenyl carbonate
DMF: N,N-dimethylformamide
MeOH: methanol
DMAP: 4-dimethylaminopyridine
DMTrCl: 4,4'-dimethoxytrityl chloride
THF: tetrahydrofuran
DAST: (diethylamino) sulfur trifluoride
(Ph)$_3$P: triphenylphosphine
Pd—C: palladium carbon
MMTrCl: 4-Methoxytriphenylmethyl chloride
DIPEA; diisopropyl ethylamine
i-Pr$_2$NP(Cl)OCE: 2-cyanoethyldiisopropylchloro-phosphoramidite unit
i-Pr$_2$ Net: diisopropylethylamine Example 1

Synthesis of 5'-amino-2'-deoxy-2'-fluorouridine amidite Unit (i) Synthesis of 2,2'-anhydro-1-β-D-arabinofuranosyluridine (1) ((1) means the compound represented by (1) in the above described Reaction Scheme A, hereinafter, same as above).
In 17 mL of DMF, 5.00 g of uridine and 5.7 g of (PhO)$_2$CO were dissolved, then 120 mg of NaHCO$_3$ was added thereto. The mixture was reacted at 130° C. for 4 hours, and after that, the reaction was terminated. After the reaction mixture washed 3 times with 30 mL each of chloroform, the solvent of the aqueous layer was evaporated. The resulting residue was dissolved in 400 mL of MeOH and recrystallized, to obtain white crystal of the compound(1) (yield: 3.58 g, 15.84 mmol, 77%).

$^1$H NMR(400 MHz)(DMSO) δ: 3.16-3.28 (m, 2H, 5'-H), 4.06 (s, 3'-H), 4.37 (d, 1H, 4'-H), 4.98 (t, 1H, J=4.80 Hz, 3'-OH), 5.18 (d, 1H, J=6.00 Hz, 2'-H), 5.83 (d, 1H, J=7.20 Hz, 5-H), 5.87 (d, 1H, J=4.40 Hz, 5'-OH), 6.29 (d, 1H, J=6.00 Hz, 1'-H), 7.83 (d, 1H, J=7.20 Hz, 6-H).

(ii) Synthesis of 2,2'-anhydro-3',5'-di-O-(4,4'-dimethoxytrityl)-1-β-D-arabinofuranosyluridine
In 68 mL of pyridine, 3 g of the compound(1) obtained in the above-described (i) and 0.4 g of DMAP were dissolved, 13.76 g of GMTrCl was then added thereto. The mixture was stirred under the argon (Ar) atmosphere. After stirring for 144 hours, the reaction was terminated by adding sat. NaHCO$_3$ ("sat." means saturated aqueous solution, hereinafter, same as above). After dilution of the reaction mixture with ethyl acetate, extraction and washing were carried out three times with 200 mL each of H$_2$O, once with 200 mL of sat. NaHCO$_3$ and once with 200 mL of sat. NaCl, then the organic layer was dried over sodium sulfate, and the solvent was removed by evaporation. The resulting residue was dissolved in 15 mL of ethyl acetate, then isolated and purified by silica gel column chromatography (hexane:ethyl acetate=9:1 to 0:1). The solvent was evaporated to obtain white crystal.

(iii) Synthesis of 3',5'-di-O-(4,4'-dimethoxytrityl)-uridine (2)
The white crystal obtained in the above-described (ii) was dissolved in 150 mL of THF, and then 40 mL of 1N NaOH was added by dropwise thereto. The reaction was conducted at 95° C. for 3 hours in an oil bath. After dilution of the reaction mixture with 80 mL of ethyl acetate, extraction and washing were carried out three times with 120 mL each of H$_2$O, once with 120 mL of sat. NaHCO$_3$ and once with 120 mL of sat. NaCl, then the organic layer was dried over sodium sulfate, and the solvent was removed by evaporation. The resulting residue was dissolved in 15 mL of ethyl acetate, then isolated and purified by silica gel column chromatography (hexane:ethyl acetate=4:1 to 0:1). The solvent was evaporated to obtain white crystal of the compound(2) (yield: 10.7 g, 43.1 mmol, 95%).

$^1$H NMR(400 MHz)(CDCl$_3$) δ: 3.51 (dd, 1H, J=14.40 Hz, 5'-H), 3.33 (d, 1H, J=9.28 Hz, 2'-OH), 3.43 (dd, 1H, J=13.44 Hz, 5'-H), 3.66 (dd, 1H, J=12.2 Hz, 2'-H), 3.93 (s, 1H, 3'-H), 4.04 (s, 1H, 4'-H), 5.58 (dd, J=10.28 Hz, 5-H), 6.09 (d, J=2.96, 1'-H), 7.14-7.35 (m, 26H, DMTr), 7.61 (d, J=8.32 Hz, 6-H), 8.35 (s, 1H, 5-NH).

(iv) Synthesis of 2'-deoxy-3',5'-di-O-(4,4'-dimethoxytrityl)-2'-fluorouridine
The compound(2) obtained in the above described (iii) was dissolved in 185 mL of CH$_3$CN under the argon (Ar) atmosphere, 14 mL of DMF was then added thereto. The reaction was initiated by adding 14 mL of DAST by dropwise under ice cooling. After 24 hours, the reaction was terminated by adding 180 mL of sat. NaHCO$_3$ under ice cooling. After dilution of the reaction mixture with ethyl acetate, extraction and washing were carried out three times with 180 mL each of H$_2$O (180 mL), once with 180 mL of sat. NaHCO$_3$ and once with 180 mL of sat. NaCl, and then the organic layer was dried over sodium sulfate, and the solvent was removed by evaporation, to obtain the residue.

(v) Synthesis of 2'-fluoro-2',5'-dideoxyuridine (3)
The residue obtained in the above described (iv) was dissolved in MeOH, 100 mL of 80% acetic acid was then added thereto. After stirring at 80° C. for 6 hours, the reaction solution was concentrated, and dissolved in 150 mL of H$_2$O. Subsequently, extraction and washing were carried out three times with 150 mL each of CHCl$_3$, then the solvent of the aqueous layer was evaporated. The resulting residue was dissolved in 15 mL of chloroform, then isolated and purified by silica gel column chromatography (chloroform: methanol=1:0 to 7:1). The solvent was evaporated to obtain white crystal of the compound(3) (yield: 1.68 g, 6.8 mmol, 58%).

$^1$H NMR(400 MHz)(DMSO) δ: 3.57 (dd, 2H, 5'-H), 3.75 (dd, J=8.00 Hz, 3'-H), 3.85-3.87 (m, 1H, 4'-H), 4.09-4.18 (m, 1H, 5-H), 4.94-5.09 (dq, 1H, 2'-H), 5.61 (dd, 1H, 5'-OH), 5.89 (dd, 1H, 1'-H), 7.90 (d, 1H, J=8.08 Hz, 6-H), 11.38 (s, 1H, 3-NH).

(vi) Synthesis of 5'-azide-2'-fluoro-2',5'-dideoxyuridine (4)

In 12 mL of DMF, 600 mg of the compound(3) obtained in the above described (v), 908 mg of (Ph)$_3$P and 793 mg of NaN$_3$ were dissolved under the argon (Ar) atmosphere, and 972 mg of CBr$_4$ was then added thereto. The reaction was conducted at 85° C. in an oil bath, and terminated the reaction after 48 hours. The reaction product was concentrated, then isolated and purified by silica gel column chromatography (chloroform:methanol=1:0 to 19:1). The solvent was evaporated to obtain white crystal of the compound(4) (yield: 0.48 g, 1.8 mmol, 73%).

$^1$H NMR(400 MHz)(DMSO) δ: 3.52 (dd, 1H, 5'-H), 3.73 (dd, 1H, 5'-H), 3.91-3.95 (m, 1H, 3'-H), 4.17-4.28 (m, 1H, 4'-H), 5.19 (dq, 1H, 2'-H), 5.65 (d, 1H, J=8.00 Hz, 3'-OH), 5.73 (d, 1H, J=6.4, 5-H), 5.85 (dd, 1H, 1'-H), 7.66 (d,1H, J=8.4, 6-H), 11.43 (s, 1H, 3-NH).

(vii) Synthesis of 5'-amino-2'-fluoro-2',5'-dideoxyuridine (5)

In 10 mL of MeOH, 507 mg of the compound(4) obtained in the above described (vi) was dissolved, and the reaction was conducted by adding 123 mg of Pd—C thereto under the H$_2$ atmosphere. After 15 hours, the reaction mixture was filtered through celite to remove Pd—C, and the solvent was evaporated to obtain white crystal of the compound(5) (yield: 0.39 mg, 1.6 mmol, 85%).

$^1$H NMR(400 MHz)(DMSO) δ: 2.82 (ddd,2H, J=3.60 Hz J=3.20 Hz J=4.80 Hz J=5.20 Hz,5'-H), 3.76 (m, 1H, 3'-H), 4.11 (ddd, 1H, J=7.20 Hz, J=7.20 Hz, J=7.20 Hz, J=7.20 Hz, 4'-H), 5.06 (ddd, 1H, J=2.00 Hz, J=2.00 Hz, J=2.40 Hz, J=2.00 Hz, 2'-H), 5.60(d,1H , J=8.00, 5-H), 5.86 (dd,1H, J=2.00 Hz, J=2.00 Hz, 1'-H), 7.91 (d, 1H, J=8.00, 6-H).

(viii) Synthesis of 5'-amino-2'-fluoro-2',5'-dideoxy-5'-N-monomethoxytrityluridine (6)

In 12 mL of pyridine, 555 mg of the compound(5) obtained in the above-described (vii) was dissolved, and 1 g of MMTrCl and 28 mg of DMAP were added thereto to conduct the reaction. After 210 hours, the reaction mixture was diluted with 40 mL of ethyl acetate, then extraction and washing were carried out three times with 40 mL each of H$_2$O, once with 40 mL of sat. NaHCO$_3$ and once with 40 mL of sat. NaCl, then the organic layer was dried over sodium sulfate, and the solvent was removed by evaporation. The resulting residue was dissolved in 5 mL of ethyl acetate, then isolated and purified by silica gel column chromatography (hexane:ethyl acetate=2:1 to 0:1), to obtain white crystal of the compound (6) (yield: 0.69 g, 1.3 mmol, 59%).

$^1$H NMR(400 MHz)(DMSO) δ: 2.43-2.70 (ddd, 2H, J=3.40 Hz, J=3.40 Hz, J=6.08 Hz, J=6.08 Hz, 5'-H), 4.06 (m, 1H, 3'-H), 5.10 (ddd,1H, 2'-H), 5.69 (d,1H, J=8.04 Hz, 5-H), 5.79 (dd, 1H,1'-H), 6.80-7.46 (17H, m, MMTr).

(ix) Synthesis of 5'-amino-N-monomethoxytrityl-2'-fluoro-2',5'-dideoxyuridine-3'-O-[(2-cyanoethyl)-(N,N-diisopropyl)]-phosphoramidite (7)

In 3.9 mL of dichloromethane (dehydrated), 400 mg of the compound(6) obtained in the above-described (viii) was dissolved, then 0.41 mL of DIPEA was added thereto and stirred. Then 0.26 mL of i-Pr$_2$NP(Cl)OCE was added by dropwise to the reaction mixture. After 1 hour, the reaction mixture was diluted with 30 mL of ethyl acetate, then extraction and washing were carried out three times with 40 mL each of H$_2$O, once with 40 mL of sat. NaHCO$_3$ and once with 40 mL of sat. NaCl. The organic layer was then dried over sodium sulfate, and the solvent was removed by evaporation. The resulting residue was dissolved in 5 mL of ethyl acetate, then isolated and purified by silica gel column chromatography (ethyl acetate), to obtain white foam-like crystal of the compound (7) (yield: 0.51 mg, 0.70 mol, 91%).

$^{31}$P NMR(400 MHz)(DMSO) δ: (151.14, 151.58).

Comparative Example 1

Synthesis of 5'-aminothymidine amidite Unit

Synthesis Scheme of 5'-aminothymidine amidite unit will be described below (Synthesis Scheme B). Formal names of the abbreviations used in the Synthesis Scheme B described below are same as above. Nucleoside derivative and amidite unit obtained by this process are not fluorinated at the 2'-position of the sugar moiety thereof.

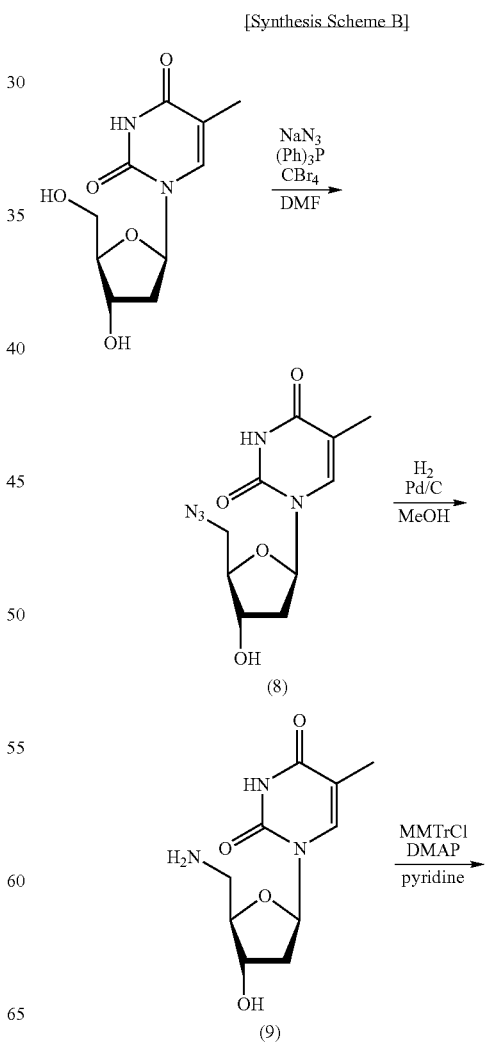

[Synthesis Scheme B]

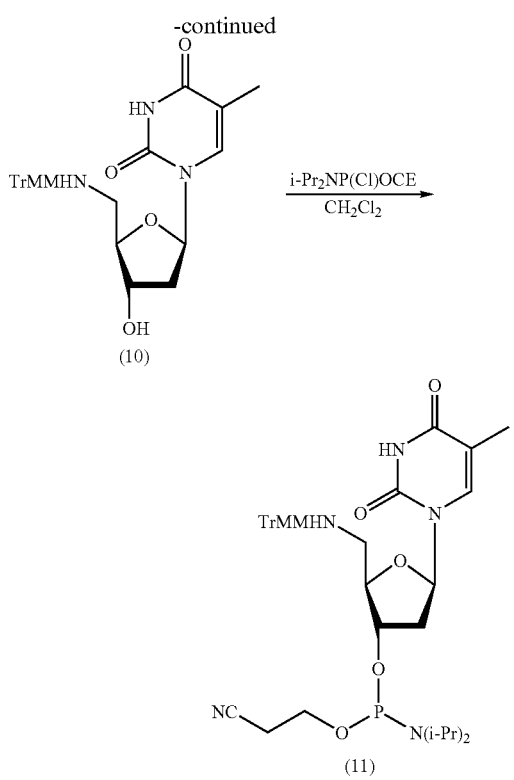

(i) Synthesis of 5'-azidethymidine (8) ((8) means the compound represented by (8) in the above described Synthesis Scheme B, hereinafter, same as above)

In 62 mL of DMF, 3 g of thymidine and 4.6 g of $(Ph)_3P$ were dissolved, then 4.9 g of $CBr_4$ was added thereto. The mixture was stirred. After 4 hours, 4.0 g of $NaN_3$ was added thereto, and the reaction was conducted at 60° C. in an oil bath. After 23 hours, the reaction mixture was concentrated using an evaporator. The concentrate was dissolved in 15 mL of chloroform, then isolated and purified by silica gel column chromatography (chloroform:methanol=1:0 to 9:1). The solvent was evaporated to obtain white crystal of the compound (8)(yield: 2.26 g, 8.46 mmol, 68%).

$^1$H NMR(400 MHz)(DMSO) δ: 1.78 (3H, s, 5-CH$_3$), 2.05-2.28 (2H, m, 2'-H), 3.54-3.55 (2H, m, 5'-H), 3.82-3.83 (1H, m, 3'-OH), 4.18 (1H, m, 4'-H), 5.40-5.41 (1H, m, 3'-H), 6.20 (1H, t J=7.00 Hz, 1'-H), 7.48 (1H, s, 6-H), 11.3 (1H, s, 3-NH).

(ii) Synthesis of 5'-aminothymidine (9)

In 84 mL of methanol, 2.26 g of the compound(8) obtained in the above-described (i) was dissolved, the reaction was conducted by adding 558 mg of Pd—C thereto under the H$_2$ atmosphere. After 13 hours, the reaction mixture was filtered through celite to remove Pd—C, and the solvent was evaporated to obtain white crystal of the compound(9) (yield: 2.02 g, 8.35 mmol, 99%).

$^1$H NMR(400 MHz)(DMSO) δ: 1.77 (s, 3H, 5-CH$_3$), 1.99-2.15 (m, 1H, 2'-H), 2.71 (d, 1H, J=5.6 Hz, 5'-H), 3.15 (s, 1H, 3'-OH), 3.63 (m, 1H, 4'-H), 4.16-4.19 (m, 1H, 3'-H), 6.27 (t, 1H, 1'-H), 7.64 (s, 1H, 6-H).

(iii) Synthesis of 5'-amino-5'-N-monomethoxytritylthymidine (10)

In 8.7 mL of pyridine, 400 mg of the compound(9) obtained in the above-described (ii) was dissolved, and 709 mg of MMTrCl and 20 mg of DMAP were added thereto to conduct the reaction. After 48 hours, the reaction mixture was diluted with 30 mL of ethyl acetate, then extraction and washing were carried out three times with 30 mL each of H$_2$O, once with 30 mL of sat. NaHCO$_3$ and once with 30 mL of sat. NaCl, then the organic layer was dried over sodium sulfate, and the solvent was removed by evaporation. The resulting residue was dissolved in 5 mL of chloroform, then isolated and purified by silica gel column chromatography (chloroform:methanol=1:0 to 23:2), to obtain white crystal of the compound(10) (yield: 715 mg, 1.39 mmol, 84%).

$^1$H NMR(400 MHz)(DMSO) δ: 1.84 (s, 3H, 5-CH$_3$), 2.05-2.15 (m, 1H, 2'-H), 2.33-2.60 (m, 1H, 5'-H), 3.97-3.99 (m, 1H, 3'-OH), 3.62 (d, 1H, 4'-H), 4.31-4.33 (m, 1H, 3'-H), 6.80-7.46 (m, 17H, MMTr), 8.43 (s, 1H, 6-H).

(iv) Synthesis of 5'-amino-N-monomethoxytritylthymidine-3'-O-[(2-cyanoethyl)-(N,N-diisopropyl)]-phosphoramidite (11)

In 2.87 mL of dichloromethane (dehydrated), 295 mg of the compound(10) obtained in the above-described (iii) was dissolved, then 0.3 mL of DIPEA was added thereto and stirred. Then 0.19 mL of i-Pr$_2$NP(Cl)OCE was added by dropwise to the reaction mixture. After 1 hour, the reaction mixture was diluted with 20 mL each of ethyl acetate, then extraction and washing were carried out three times with 20 mL of H$_2$O, once with 20 mL of sat. NaHCO$_3$ and once with 20 mL each of sat. NaCl. The organic layer was then dried over sodium sulfate, and the solvent was removed by evaporation. The resulting residue was dissolved in 5 mL of ethyl acetate, then isolated and purified by silica gel column chromatography (ethyl acetate), to obtain white foam-like crystal of the compound(11) (yield: 357 mg, 0.752 mmol, 87%).

$^{31}$P NMR(400 MHz)(DMSO) δ: (149.58, 149.83).

Example 2

Synthesis of Oligonucleotide by Solid Phase Phosphoramidite Method

Oligonucleotide analogue being introduced with 5'-amino-2'-fluoro-2',5'-dideoxyuridine of the present invention was synthesized according to the method described below.

First, as materials, 5'-amino-N-monomethoxytrityl-2'-fluoro-2',5'-dideoxyuridine-3'-O-[(2-cyanoethyl)-(N,N-diisopropyl)]-phosphoramidite (7) synthesized in Example 1, commercially available dA-CE phosphoramidite [chemical name: (5'-Dimethoxytrityl-N-benzoyl-2'-deoxyAdenosine, 3'-[(2-cyanoethyl)-(N,N-diisopropyl)]-phosphoramidite)] and dG-CE phosphoramidite [chemical name: 5'-Dimethoxytrityl-N-isobutyryl-2'-deoxyGuanosine, 3'-[(2-cyanoethyl)-(N,N-diisopropyl)]-phosphoramidite] (both produced by Glen research Corp.) were used. In addition, as a starting material, 3'-dA-CPG (CPG means Controlled Pore Glass, and produced by Glen research Corp.) (1 μmol) packed in a column was used.

An oligonucleotide analogue was synthesized using 3400 DNA Synthesizer (a nucleic acid synthesizer produced by Applied Biosystems) as a synthesizer, and using these materials and an starting material described above.

The two kinds of oligonucleotide analogues obtained were analyzed for their structures by MALDI TOF/MAS using AXIMA (produced by Shimadzu Corp.).

The two kinds of oligonucleotide analogues obtained were named as UNF-1 and UNF-2. The base sequence of UNF-1 (SEQ ID NO:1), base sequence of NF-2 (SEQ ID NO:2), theoretical values (calculated) and observed values (observed) of molecular weights thereof are shown in Table 1. In the base sequences in Table 1, the position where 5'-amino-2'-fluoro-2',5'-dideoxyuridine has been introduced is indicated as $U^{NF}$.

TABLE 1

| | Sequence | calculated | observed |
|---|---|---|---|
| Example 2 | | | |
| UNF-1 | SEQ ID NO: 1 | 5'-(AAG GAA AU$^{NF}$G AGG AAA GA)-3' | 5352.5 | 5351.4 |
| UNF-2 | SEQ ID NO: 2 | 5'-(AAG GAA U$^{NF}$U$^{NF}$G AGG AAA GA)-3' | 5347.5 | 5347.2 |
| Comparative Example 2 | | | |
| TN-1 | SEQ ID NO: 3 | 5'-(AAG GAA AT$^{N}$G AGG AAA GA)-3' | 5348.6 | 5347.7 |
| TN-2 | SEQ ID NO: 4 | 5'-(AAG GAA T$^{N}$T$^{N}$G AGG AAA GA)-3' | 5337.6 | 5337.8 |
| T-1 (control) | SEQ ID NO: 5 | 5'-d(AAG GAA ATG AGG AAA GA)-3' | — | — |
| T-2 (control) | SEQ ID NO: 6 | 5'-d(AAG GAA TTG AGG AAA GA)-3' | — | — |

Comparative Example 2

Two kinds of oligonucleotide analogues were synthesized according to the same method as in Example 2, except that 5'-amino-N-monomethoxytritylthymidine-3'-O-[(2-cyanoethyl)-(N,N-diisopropyl)]-phosphoramidite (11) synthesized in Comparative Example 1 was used as a material in place of 5'-amino-N-monomethoxytrityl-2'-fluoro-2',5'-dideoxy-uridine-3'-O-[(2-cyanoethyl)-(N,N-diisopropyl)]-phosphoramidite (7) synthesized in Example 1.

The two kinds of oligonucleotide analogues obtained were named as TN-1 and TN-2. In addition, confirmations of their structures were performed according to the same method as in Example 2 by MALDI TOF/MAS. The base sequences of TN-1 (SEQ ID NO:3) and TN-2 (SEQ ID NO:4), theoretical values (calculated) and observed values (observed) of molecular weights of both analogues are shown together in Table 1. In the base sequences in Table 1, the position, where 5'-aminothymidine has been introduced, is indicated as $T^N$.

In addition, using commercially available dT-CE phosphoramidite [chemical name: 5'-Dimethoxytrityl-2'-deoxyThymidine, 3'-[(2-cyanoethyl)-(N,N-diisopropyl)]-phosphoramidite], dA-CE phosphoramidite, dG-CE phosphoramidite (all of them were produced by Glen research Corp.) as materials, also using 3'-dA-CPG 500 (1 μmol) column packed with 3'-dA-CPG (produced by Glen research Corp.) as a starting material, oligonucleotides were synthesized according to the same method as in Example 2 to obtain oligonucleotides comprising only naturally occurring nucleosides. The two kinds of oligonucleotides obtained were named as T-1 (control) and T-2 (control). In addition, confirmations of their structures were carried out according to the same method as in Example 2 by MALDI TOF/MAS. The base sequences of T-1 (control) (SEQ ID NO:5) and T-2 (control) (SEQ ID NO:6) are shown together in Table 1.

Example 3

Measurement of Tm (Melting Temperature) (DNA/DNA Match Duplex)

(i) Synthesis of Complementary Oligonucleotide

Using commercially available dT-CE phosphoramidite and dA-CE phosphoramidite (both of them were produced by Glen research Corp.) as materials, also using 3'-dT-CPG (1 μmol) packed in a column (produced by Glen research Corp.) as a starting material, oligonucleotides were synthesized according to the same method as in Example 2, in order to obtain oligonucleotides which were each complementary to UNF-1 and UNF-2 obtained in Example 2, respectively. The base sequences of oligonucleotides complementary to UNF-1 (SEQ ID NO:7) and complementary to UNF-2 (SEQ ID NO:8) are shown in Table 2 below.

TABLE 2

| SEQ ID NO: 7 | 3'-d(TTC CTT TAC TCC TTT CT)- 5' |
|---|---|
| SEQ ID NO: 8 | 3'-d(TTC CTT AAC TCC TTT CT)- 5' |

(ii) Thermal Stability Test

Using UNF-1 and UNF-2, which were synthesized in Example 2, and complementary oligonucleotides thereto shown in Table 2 as materials, duplexes DNA/DNA were prepared according to the conventional method (R. Kierzek et al., Biochemistry, 1986, vol. 25, pp. 7840-7846).

Using the obtained duplex DNA/DNA, thermal stability test was carried out according to the conventional method.

That is, using a UV-2450 SPECTROPHOTOMETER equipped with a temperature-variable device (produced by Shimadzu Corp.), the oligonucleotides were placed in 8 consecutive 10 mm cells under the nitrogen atmosphere, and 10 mM of sodium phosphate buffer and 100 mM of sodium chloride (pH 7.0) were added thereto so that the concentration of each oligonucleotide became 3 μM, then the temperature was increased from 20° C. to 90° C. with a climbing rate of 0.5° C. per minute, and absorbance at 260 nm were measured.

The results are shown in FIG. 1.

In FIG. 1, closed circle (●) indicates the results on the duplex DNA/DNA obtained by using UNF-1; open circle (○) indicates the results on the duplex DNA/DNA obtained by using UNF-2.

Also, Tm and ΔTm of each duplex DNA/DNA obtained from the results shown in FIG. 1 are shown in Table 3.

TABLE 3

| | | Tm | ΔTm |
|---|---|---|---|
| ▲ | T-1 (control) | 52.9 | — |
| △ | T-2 (control) | 53.5 | — |
| ● | UNF-1 | 51.8 | −1.1 |
| ○ | UNF-2 | 52.1 | −1.4 |
| ■ | TN-1 | 50.6 | −2.3 |
| □ | TN-2 | 48.3 | −5.2 |

Comparative Example 3

Measurement of Tm (DNA/DNA Match Duplex)

A duplex DNA/DNA formed between TN-1 synthesized in Comparative Example 2 and a complementary oligonucleotide thereto represented by SEQ ID NO:7, and a duplex formed DNA/DNA between TN-2 synthesized in Comparative Example 2 and a complementary oligonucleotide thereto represented by SEQ ID NO:8 were synthesized according to the same method as in Example 3. The thermal stability of these duplex nucleic acids obtained was examined according to the same method as in Example 3.

The results are shown together in FIG. 1.

In FIG. 1, closed square (■) indicates the results on the duplex DNA/DNA obtained by using TN-1; open square (□) indicates the results on the duplex DNA/DNA obtained by using TN-2.

Also, Tm and ΔTm of each duplex DNA/DNA obtained from the results shown in FIG. 1 are shown together in Table 3.

In addition, a duplex DNA/DNA formed between T-1 (control) synthesized in Comparative Example 2 and a complementary oligonucleotide thereto represented by SEQ ID NO:7, and a duplex DNA between T-2 (control) synthesized in Comparative Example 2 and a complementary oligonucleotide thereto represented by SEQ ID NO:8 were synthesized according to the same method as in Example 3. Thermal stability of these duplex nucleic acids obtained was examined according to the same method as in Example 3. The results were shown together in FIG. 1.

In FIG. 1, closed triangle (▲) indicates the results on the duplex DNA/DNA obtained by using T-1 (control); open triangle (Δ) indicates the results on the duplex DNA/DNA obtained by using T-2 (control).

Also, Tm of each duplex DNA/DNA obtained from the results shown in FIG. 1 is shown together in Table 3.

As is clear from the results shown in FIG. 1 and Table 3, the Tm of the duplex DNA/DNA containing oligonucleotide analogues (UNF-1 and UNF-2) being introduced with 5'-amino-2'-fluoro-2',5'-dideoxyuridine of the present invention is equivalent to that of the duplex DNA/DNA comprising oligonucleotide (T-1 (control) and T-2 (control)) comprising only naturally occurring type nucleosides. This means that thermal stabilities of both duplex nucleic acids are equivalent. On the other hand, the Tm of the duplex DNA/DNA comprising oligonucleotide analogues (TN-1 and TN-2) being introduced with 5'-aminothymidine, in which the 2'-position of the sugar moiety was not fluorinated, is lower than that obtained for the duplex DNA/DNA comprising oligonucleotide (T-1 (control) and T-2 (control)) comprising only naturally occurring type nucleosides, and thus, it is clear that thermal stability of these duplex nucleic acids are low.

Example 4

Measurement of Tm (DNA/RNA Match Duplex)

(i) Synthesis of Complementary Oligonucleotide

Using commercially available rA-CE phosphoramidite, rU-CE phosphoramidite and rC-CE phosphoramidite as materials, also using 3'-dU-CPG (all of them were produced by Glen research Corp.) as a starting material, complementary oligonucleotides to each of UNF-1 and UNF-2 which were prepared in Example 2, were synthesized according to the same method as in Example 2.

The base sequences of oligonucleotides complementary to UNF-1 (SEQ ID NO:9) and complementary to UNF-2 (SEQ ID NO:10), are shown in Table 4 below.

TABLE 4

SEQ ID NO: 9    3'-r(UUC CUU UAC UCC UUU CU)- 5'

SEQ ID NO: 10   3'-r(UUC CUU AAC UCC UUU CU)- 5'

(ii) Thermal Stability Test

Using UNF-1 and UNF-2, which were synthesized in Example 2, and the complementary oligonucleotides thereto shown in Table 2 as materials, a duplex DNA/RNA was prepared according to the conventional method (R. Kierzek et al., Biochemistry, 1986, vol. 25, pp. 7840-7846).

Using the obtained duplexes DNA/RNA, thermal stability test was carried out according to the same method as in Example 3.

The results are shown in FIG. 2.

In FIG. 2, closed circle (●) indicates the results on the duplex DNA/RNA obtained by using UNF-1; open circle (○) indicates the results on the duplex DNA/RNA obtained by using UNF-2.

Also, Tm and ΔTm of each duplex DNA/RNA obtained from the results shown in FIG. 2 are shown in Table 5.

TABLE 5

|   |   | Tm | ΔTm |
|---|---|---|---|
| ▲ | T-1 (control) | 42.1 | — |
| Δ | T-2 (control) | 44.0 | — |
| ● | UNF-1 | 41.9 | −0.2 |
| ○ | UNF-2 | 43.5 | −0.5 |
| ■ | TN-1 | 37.7 | −4.4 |
| □ | TN-2 | 39.0 | −5.0 |

Comparative Example 4

Measurement of Tm (DNA/RNA Match Duplex)

A duplex DNA/RNA formed between TN-1 synthesized in Comparative Example 2 and a complementary oligonucleotide thereto represented by SEQ ID NO:9, and a duplex DNA/RNA formed between TN-2 synthesized in Comparative Example 2 and a complementary oligonucleotide thereto represented by SEQ ID NO:10 were synthesized according to the same method as in Example 4. Thermal stabilities of these duplex nucleic acids obtained were examined according to the same method as in Example 4.

The results are shown together in FIG. 2.

In FIG. 2, closed square (■) indicates the results on the duplex DNA/RNA obtained by using TN-1; open square (□) indicates the results on the duplex DNA/RNA obtained by using TN-2.

Also, Tm and ΔTm of each duplex DNA/RNA obtained from the results shown in FIG. 2 are shown together in Table 5.

In addition, a duplex DNA/RNA formed between T-1 (control) synthesized in Comparative Example 2 and a complementary oligonucleotide thereto represented by SEQ ID NO:9, and a duplex DNA formed between T-2 (control) synthesized in Comparative Example 2 and a complementary oligonucleotide thereto represented by SEQ ID NO:10 were synthesized according to the same method as in Example.

Thermal stabilities of these duplex nucleic acids obtained were examined according to the same method as in Example 4.

The results are shown together in FIG. 2.

In FIG. 2, closed triangle (▲) indicates the results on the duplex DNA/RNA obtained by using T-1 (control); open triangle (Δ) indicates the results on the duplex DNA/RNA obtained by using T-2 (control).

Also, Tm of each duplex DNA/RNA obtained from the results shown in FIG. 2 is shown together in Table 5.

As is clear from the results shown in FIG. 2 and Table 5, the Tm of the duplex DNA/RNA comprising oligonucleotide analogues (NF-1 and UNF-2) being introduced with 5'-amino-2'-fluoro-2',5'-dideoxyuridine of the present invention is equivalent to that of the duplex DNA/RNA comprising oligonucleotide (T-1 (control) and T-2 (control)) comprising only naturally occurring type nucleosides. This means that thermal stabilities of both duplex nucleic acids are equivalent. On the other hand, the Tm of the duplex DNA/RNA comprising oligonucleotide analogues (TN-1 and TN-2) being introduced with 5'-aminothymidine, in which the 2'-position of the sugar moiety was not fluorinated, is lower than that obtained for the duplex DNA/RNA comprising oligonucleotide (T-1 (control) and T-2 (control)) comprising only naturally occurring type nucleosides, and thus, it is clear that thermal stability of these duplex nucleic acids are low.

In addition, as is clear from the results shown in Table 3 and Table 5, the Tm of UNF-2 which contains two UNFs is higher than that of UNF-1 which contains one UNF. It is, therefore, anticipated that stability of duplex nucleic acid can be further improved by increasing the number of the dideoxynucleoside derivative of the present invention being introduced into an oligonucleotide.

INDUSTRIAL APPLICABILITY

The 5'-amino-2'-fluoro-2',5'-dideoxynucleoside derivatives of the present invention can be used as a phosphoramidite reagent to be used for nucleic acid synthesis, and also as a starting material for solid phase synthesis of nucleic acid by binding (immobilizing) the aforementioned dideoxynucleoside derivatives to a solid phase. Also, the oligonucleotide analogues being introduced with the aforementioned derivatives are anticipated to have excellent thermal stability and high resistance to nucleases.

Therefore, the aforementioned oligonucleotide analogues can be used in the antisense method as an excellent antisense nucleic acid having resistance to nucleases. Also, the aforementioned oligonucleotide analogues can be used as dsRNA and siRNA to be introduced into cells in the RNAi method. Further, the aforementioned oligonucleotide analogues can be used as an antisense oligonucleotide analogue to be used in the method of knocking out a target gene. Furthermore, application to pharmaceutical field and utilization as a probe for analyzing genetic polymorphism may also be anticipated.

What is claimed is:

1. A 5'-amino-2'-fluoro-2',5'-dideoxynucleoside compound represented by the following formula [1]:

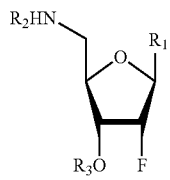

[1]

wherein $R_1$ represents a nucleic acid base which may have a protecting group; $R_2$ represents a hydrogen atom or an amino protecting group; and $R_3$ represents a hydrogen atom or a hydroxyl protecting group.

2. The compound of claim 1, wherein the 5'-amino-2'-fluoro-2',5'-dideoxynucleoside compound represented by the formula [1] is a compound represented by the following formula [3]:

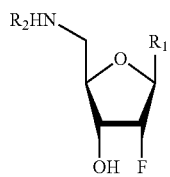

[3]

wherein $R_1$ represents a nucleic acid base which may have a protecting group; and $R_2$ represents a hydrogen atom or an amino protecting group.

3. The compound of claim 1, wherein the 5'-amino-2'-fluoro-2',5'-dideoxynucleoside compound represented by the formula [1] is a compound represented by the following formula [5]:

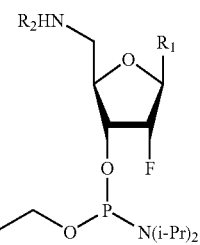

[5]

wherein $R_1$ represents a nucleic acid base which may have a protecting group; $R_2$ represents a hydrogen atom or an amino protecting group; and i-Pr represents an isopropyl group.

4. A dideoxynucleoside-insoluble carrier bound substance that is a 5'-amino-2'-fluoro-2',5'-dideoxynucleoside compound represented by the following formula [6]:

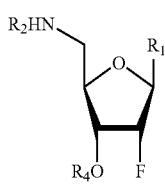

[6]

wherein $R_1$ represents a nucleic acid base which may have a protecting group; $R_2$ represents a hydrogen atom or an amino protecting group; and $R_4$ represents a solid support with a linker moiety.

5. An oligonucleotide analogue comprising a 5'-amino-2'-fluoro-2',5'-dideoxynucleoside monomeric unit represented by the following formula [1]:

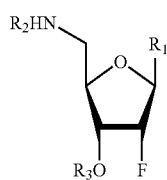

[1]

wherein $R_1$ represents a nucleic acid base which may have a protecting group; $R_2$ represents a hydrogen atom or an amino protecting group; and $R_3$ represents a hydrogen atom or a hydroxyl protecting group, wherein an oligonucleoside chain or oligonucleotide chains are attached via chemical linkage in place of one or both of substituent groups $R_2$ and $R_3$ of formula [1].

6. The oligonucleotide analogue of claim 5, wherein the chemical linkage is a phosphate diester linkage or a phosphormonoamidate-monoester linkage.

* * * * *